(12) United States Patent
Gurm

(10) Patent No.: US 8,287,585 B2
(45) Date of Patent: Oct. 16, 2012

(54) OSTIAL STENTING SYSTEM

(75) Inventor: Hitinder Gurm, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 531 days.

(21) Appl. No.: 12/344,034

(22) Filed: Dec. 24, 2008

(65) Prior Publication Data

US 2009/0198178 A1 Aug. 6, 2009

Related U.S. Application Data

(60) Provisional application No. 61/016,747, filed on Dec. 26, 2007.

(51) Int. Cl.
*A61F 2/84* (2006.01)
(52) U.S. Cl. ...................... 623/1.11; 606/194
(58) Field of Classification Search ............... 623/1.11, 623/1.12, 1.23, 23.7; 606/198, 108, 194, 606/200; 604/103.05, 103.09, 104, 96.01, 604/103.1
See application file for complete search history.

(56) References Cited

U.S. PATENT DOCUMENTS

| | | | |
|---|---|---|---|
| 5,651,047 A | 7/1997 | Moorman et al. | |
| 5,776,142 A | 7/1998 | Gunderson | |
| 5,928,248 A | 7/1999 | Acker | |
| 6,080,171 A * | 6/2000 | Keith et al. | 606/159 |
| 6,102,940 A | 8/2000 | Robichon et al. | |
| 6,139,524 A | 10/2000 | Killion | |
| 6,261,273 B1 | 7/2001 | Ruiz | |
| 6,440,097 B1 | 8/2002 | Kupiecki | |
| 6,540,734 B1 | 4/2003 | Chiu et al. | |
| 6,623,491 B2 | 9/2003 | Thompson | |
| 6,730,119 B1 | 5/2004 | Smalling | |
| 6,746,476 B1 | 6/2004 | Hojeibane | |
| 6,749,627 B2 | 6/2004 | Thompson et al. | |
| 6,827,718 B2 | 12/2004 | Hutchins et al. | |
| 6,872,192 B2 | 3/2005 | Nash et al. | |
| 6,989,024 B2 | 1/2006 | Hebert et al. | |
| 7,105,019 B2 | 9/2006 | Hojeibane | |
| 7,163,504 B1 | 1/2007 | Chiu et al. | |
| 7,753,951 B2 * | 7/2010 | Shaked et al. | 623/1.35 |
| 2006/0259116 A1 * | 11/2006 | Feld et al. | 623/1.11 |
| 2007/0173918 A1 * | 7/2007 | Dreher et al. | 623/1.11 |
| 2007/0203562 A1 * | 8/2007 | Malewicz et al. | 623/1.11 |

OTHER PUBLICATIONS

Colombo, et al., "Selection of Coronary Stents," Journal of the American College of Cardiology, 40(6):1021-1033 (2002).

* cited by examiner

*Primary Examiner* — Kathleen Sonnett
(74) *Attorney, Agent, or Firm* — Marshall, Gerstein & Borun LLP

(57) ABSTRACT

A method and apparatus provide techniques for stenting ostial legions and other restenosis in vessels through a stenting apparatus that includes both a guidewire and a separate marker wire. In some examples, the marker wire is threaded through a tubular body of the stenting apparatus and in other examples, the marker wire may be threaded externally through the tubular body. In both such examples, the marker wire may be aligned with a radiopaque marker of the apparatus to guide marker wire positioning.

9 Claims, 6 Drawing Sheets

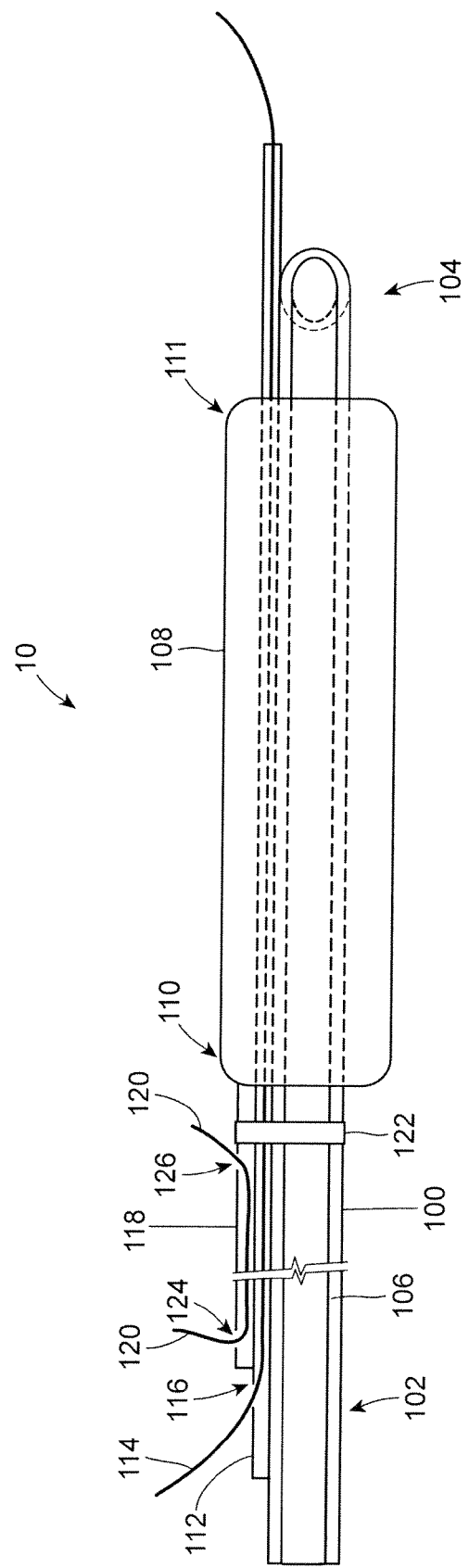

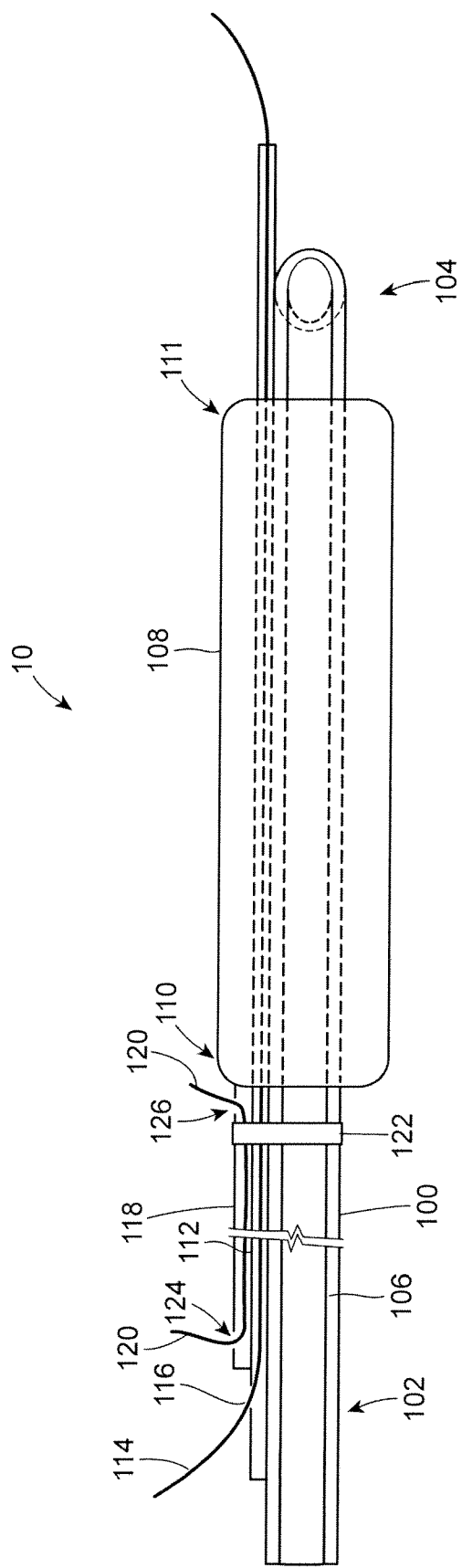

OSTIAL STENTING SYSTEM

CROSS REFERENCE TO RELATED APPLICATIONS

The present application claims the benefit of U.S. Provisional Application No. 61/016,747, entitled "An Ostial Stenting System", filed on Dec. 26, 2007, which is hereby incorporated by reference herein in its entirety.

FIELD OF THE INVENTION

The present invention relates generally to devices for stenting lesions within a vascular region and more particularly to devices for stenting ostial lesions in a bifurcation vessel.

BACKGROUND OF THE RELATED ART

Atherosclerosis and cardiovascular disease are leading causes of mortality and morbidity worldwide. Each process can affect major and minor arterial vessels. Yet while arterial and venous thrombosis have numerous origins, it is at the end organs where the effects of the thrombosis are most felt and where those effects result in clinical manifestation. Arterial thrombosis, for example, may manifest as sudden cardiac death, acute coronary syndromes (ACS), stroke, or peripheral embolization. Venous thrombosis may manifest as acute deep vein thrombosis (DVT), pulmonary embolism (PE), or paradoxical arterial embolization.

The underlying causes of these manifestations range from atherosclerosis due to plaque rupture or erosion (e.g., sudden death, ACS, etc), cardiac embolization from atrial fibrillation or left ventricular aneurysm (often secondary to coronary atherosclerosis), stasis and immobility (e.g., postoperative DVT), hypercoagulable state (activated protein C deficiency, malignancy), and a variety of rare disorders. Furthermore, thrombosis may complicate the performance of cardiovascular procedures or initiate malfunction of foreign devices implanted in the cardiovascular system (heart valves, arterial stents, venous filters, bypass grafts, etc).

Given the deleterious impact of atherosclerosis, various interventions have been developed to reduce or remove blockages in blood vessels. One technique for treating stenosis or occlusion of a blood vessel is balloon angioplasty. A balloon catheter is inserted into the narrowed or blocked area, and the balloon is inflated to expand the constricted area. While commonly performed, this method is not without risk. Angioplasty can be associated with significant plaque shift, arterial dissection and high risk of restenosis.

Coronary bypass surgery is another more costly and invasive form of intervention, in which a section of a vein, such as the saphenous vein taken from the leg, is used to form a connection between the aorta and the coronary artery distal to the obstruction. Though common, this intervention is not without challenges. Over time, the saphenous vein graft may itself become diseased, stenosed, or occluded similar to the bypassed vessel, which can present a different problem, as atherosclerotic plaque in saphenous vein grafts tends to be more friable and less fibrocalcific than its counterpart in native coronary arteries.

Various types of stents have been designed to address the problems of restenosis discussed above, generally with good success. However, while the stents have, in many ways, revolutionized the field of vascular interventions, significant challenges remain. Bifurcations and ostial lesions, for example, present unique problems to surgeons during a stenting procedure. In coronary and non-coronary beds, the ostial location is prone to develop atherosclerosis and is therefore the most common site of disease in renal vessels and is a common site of disease in patients with saphenous vein graft disease or those with coronary artery disease. In endovascular treatment of ostial lesions, it is desirable to adequately cover the entire vessel ostium but to do so without leaving excessive stent protruding from the ostial vessel into the aorta or main vessel. This is desirable for a number of reasons. If the ostium is missed, there is a high risk of restenosis. Further still, if the ostium is missed, it is difficult to identify which portion of the entire opening has been affected and which has not, thus requiring an entirely new stenting procedure and possibly a new stent altogether. Another problem is that if the stent protrudes too far into the aorta or main vessel, it will become difficult to subsequently re-engage the vessel with a diagnostic catheter. Although there is a low risk of restenosis from having the stent extending too far into the main vessel, the procedure is made more difficult because the catheter guide wire will often go through a strut member limiting the effectiveness of the guidewire for the catheter upon entry and removal. Thus, future interventions are made difficult or next to impossible to implement.

The most common ostial intervention sites, including bifurcation points, are aortic-coronary ostia and renal ostia. The standard angioplasty balloon used for such sites is a semi-compliant or non-compliant balloon that is fixed to a balloon shaft and can be expanded and deflated as is in routine interventional practice. The balloon will often have radiopaque markers that are used to identify the proximal and distal ends of the balloon and that serve to guide the location of the proximal and distal edge of the stent. Radiographic location techniques, using multiple angulations and contrast, identify, the ostium of the vessel. This practice unfortunately translates into extra-radiation to the patient and the operator and also carries the burden of increased contrast and prolonged occlusion of the vessel. This practice also increases the risk of the procedure failing especially for patients undergoing interventions on ostia of the main coronary arteries or ostia of the saphenous vain grafts. In patients with renal dysfunction, for example, the extra contrast volume and radiation exposure can translate into renal failure and the need for dialysis.

In any event, there is a need for improved stenting devices for ostial lesions, in particular, and at bifurcation points to allow more accurate alignment of the stent so as to cover the entire ostium and also control the extent to which the stent extends into the main vessel.

SUMMARY OF THE INVENTION

In accordance with an example, a catheter device for administering a stent in an ostial vessel, includes: an expandable balloon have a proximal end and a distal end, the expandable balloon having an inflation channel extending past the proximal end for delivering inflation pressure to the expandable balloon; a catheter guidewire channel extending from a proximal end of the catheter device to a distal end of the catheter device, the distal end of the catheter device extending past the distal end of the expandable balloon and providing a pathway for the catheter guidewire; a radiopaque marker positioned proximal to the proximal end of the expandable balloon; and a marker wire channel adjacent the catheter guidewire channel and extending to the radiopaque marker, the marker wire channel having a exit opening at the radiopaque marker for pulling a marker wire extending through the marker wire channel out of the marker wire channel proximal to the expandable balloon.

In accordance with another example, a catheter device for administering a stent in an ostial vessel, includes: an expandable balloon have a proximal end and a distal end, the expandable balloon having an inflation channel extending past the proximal end for delivering inflation pressure to the expandable balloon; a catheter guidewire channel extending from a proximal end of the catheter device to a distal end of the catheter device, the distal end of the catheter device extending past the distal end of the expandable balloon and providing a pathway for the catheter guidewire; and a radiopaque marker positioned proximal to the proximal end of the expandable balloon, the radiopaque marker having ring channel external to a tubular body of the catheter device, the ring channel defining an opening for receiving a marker wire proximal to the expandable balloon.

In accordance with yet another example, a method of forming a stent for insertion into an ostial vessel, includes: providing a balloon catheter device comprising a tubular body having an inflation channel and a catheter guidewire channel and an expandable balloon surrounding the tubular body and positioned to inflate in response to inflation pressure to the inflation channel, the catheter guidewire channel extending from a proximal end of the expandable balloon to a distal end of the expandable balloon; disposing a radiopaque marker proximal to the proximal end of the expandable balloon; threading a marker wire through a channel adjacent the catheter guidewire channel and having a exit opening at the radiopaque marker for threading the marker wire out of the marker wire channel proximal to the expandable balloon; and disposing an expandable stent around the expandable balloon.

In accordance with another example, a method of forming a stent for insertion into an ostial vessel, includes: providing a balloon catheter device comprising a tubular body having an inflation channel and a catheter guidewire channel and an expandable balloon surrounding the tubular body and positioned to inflate in response to inflation pressure to the inflation channel, the catheter guidewire channel extending from a proximal end of the expandable balloon to a distal end of the expandable balloon; disposing a radiopaque marker proximal to the proximal end of the expandable balloon, the radiopaque marker having ring channel external to the tubular body, the ring channel defining an opening for threading a marker wire through the ring channel for assistance in positioning the balloon catheter device in the ostial vessel; and disposing an expandable stent around the expandable balloon.

BRIEF DESCRIPTION OF THE DRAWINGS

FIG. 1 illustrates a catheter apparatus having a marker wire channel internal to a tubular body of the apparatus in accordance with an example;

FIG. 2 illustrates a catheter apparatus similar to that of FIG. 1 but in accordance with another example;

DESCRIPTION OF DETAILED EXAMPLES

Figure 3A:
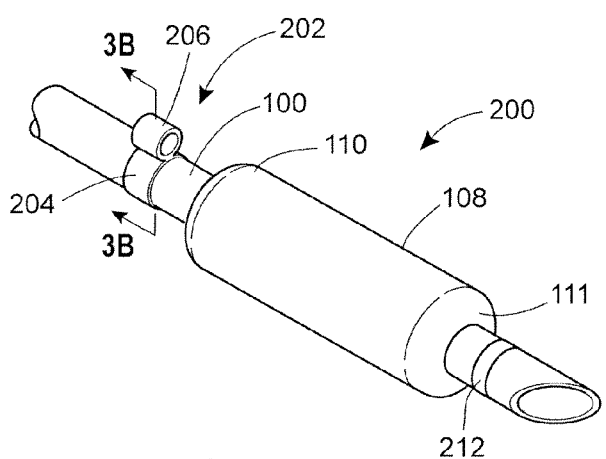
FIGS. 3A and 3B illustrate a perspective view and cross-section view, respectively, of a portion of another catheter apparatus having a radiopaque marker defining a marker channel.

The angioplasty and stenting catheter apparatuses and techniques described herein address the various problems described above. Some of these apparatuses described are capable of accomplishing the twin purposes of providing adequate ostio coverage and minimizing any excess stent extending into the parent vessel. These examples may be achieved by low-profile apparatuses that avoid the limitations attributable to current devices. Generally speaking, the apparatuses may include structures for inserting and inflating angioplasty balloons as well as structures to pull stents at balloon sites. The balloons may be monorail angioplasty balloons coupled with a therapeutic channel such as that as described in pending U.S. Ser. No. 11/935,131, entitled "Angioplasty Balloon with Therapeutic/Aspiration Channel" incorporated herein by reference. The apparatuses may be used to deliver therapeutic or aspiration functionality before, during or after balloon inflation or deflation as necessary.

A single catheter may include an angioplasty balloon on the shaft and a guidewire channel that runs along the entire or partial length of that shaft and is used, as in traditional systems, to guide positioning of the balloon for inflation and/or stent insertion. In accordance with the present teachings, a separate marker wire is used in addition to the catheter guidewire. The marker wire may be positioned in a separate channel or assembly than that of the guidewire and may be freely controllable with respect to the guidewire. That is, the marker wire may be used to provide further adjustment during catheter apparatus deployment by providing a separate wire control from that of the guidewire, and by (in some examples) further providing additional wire control on a proximal side of the balloon or stent delivery portion of the catheter, while the guidewire extends onto a distal side of the balloon or stent delivery portion. In some examples, the marker wire may be fed directly through a radiopaque marker, while in other examples the marker wire may extend along and parallel to a balloon inflation channel with an opening either proximally or distally to the radiopaque marker. In either case, the marker wire may be made to travel within a portion of the catheter apparatus that is identified by a radiopaque marker, and thus may provide an effective technique for not only identifying the position of the angioplasty balloon, and therefore the position of the stent, but also for identifying guidewire positions from which a surgeon can better ensure ostial coverage and main vessel clearance. The wires of the present application may be combined with a therapeutic/aspiration channel that administers a local therapeutic to a treated region or aspirates body fluids and emboli, thrombi, and other particles.

With the present techniques, the catheter apparatuses may be provided in either over-the-wire or in single operator form. Radiopaque markers may be incorporated into the distal ends of the catheters to facilitate their positioning within the body. The catheters may be provided with varying flexibility along the length of the shaft, such that they are soft and flexible enough to be navigated through the vasculature of a patient without causing damage, but are stiff enough to sustain the axial push required to position the catheter properly and to sustain the aspiration pressures.

FIG. 1 illustrates an example catheter apparatus 10 that comprises an elongate flexible tubular body 100 having a proximal end 102 and a distal end 104. The catheter body may incorporate a reinforcement (not shown) such as a metallic braid or coil or a polymer coil to provide enough strength and flexibility to the device and inflation lumen (channel) 106.

The reinforcement for the tubular body 100 can be formed from a variety of materials, including polymers, stainless steel, silver or gold plated stainless steel, platinum, nitinol, or a combination thereof. The distal end 104 of the catheter body 100 is preferably more flexible than the proximal end 102, and may be more flexible then the rest of tubular body 100. In addition to using different materials for the catheter, flexibility may be achieved by providing a braid or coil density at the distal end which is greater or lesser than the braid or coil density, at the proximal end.

The catheter apparatus further includes an angioplasty expandable balloon 108 having a proximal end 110 and a distal end 111 where the inflation channel 106 extends from the proximal end of the tubular body 102, in the illustrated example, at least as far as the distal end 111 to inflate the expandable balloon. In the illustration of FIG. 1, the balloon 108 is shown in a partially expanded configuration. The balloon may be further expanded by the provision of additional fluid to the inflation channel 106. Furthermore, in a fully non-deployed configuration, the balloon would be deflated and employ a diameter closer to that of the tubular body 100.

The angioplasty catheter includes a second lumen 112, adjacent the inflation channel 106 (in cross-section) and adapted to receive a guidewire 114. This guidewire lumen 112 may extend substantially the entire length of the tubular body 100 or (as shown in FIG. 1) may extend distally from the end 104. For example, the guidewire lumen 112 may extend beyond the distal end 104 by approximately 40 mm, approximately 20 mm, or smaller distances as desired. The second lumen 112 may contain a slit or opening 116 through a side wall to allow insertion and removal of the guidewire. In an example, the second lumen 112 has an inner diameter of approximately 0.020 inches to receive a 0.014 inch diameter guidewire. More generally, in some examples, the lumen 112 may have any inner diameter over a range of approximately 0.008 inches to approximately 0.038 inches. To provide further examples, the maximum profile of the apparatus 10 pre-balloon inflation may be 1.8 mm at the proximal end 102 and 0.9 mm beyond the distal end to the channel. The guidewire lumen 112 may be formed of a shaft length of 135 cm, for example, with the guidewire exiting at 30 cm beyond the distal end 104. The balloon 108 may be approximately 5.5 or 6 mm diameter balloon approximately 20 mm in length for large vessels or approximately 2.5 or 3 mm diameter balloon approximately 12 to 15 mm in length for moderate size vessels. These numbers are provided for example purposes.

In addition to the inflation channel 106 and the guidewire channel 112, the catheter apparatus 10 also includes a separate channel 118 for a marker wire 120. The channel 118 is adjacent the catheter guidewire channel 112 in the illustrated configuration and extends from the proximal end 102 to a radiopaque marker 122 positioned proximal to the proximal end 110 of the expandable balloon 108. The channel 118 has an entry opening 124 for receiving the marker wire 120, and an exit opening 126, which in the illustrated example, is at the radiopaque marker 122. In some examples, the exit opening 126 may be proximal to the marker 122, while in other examples, the exit opening 126 may be distal to the marker 122. In either case, the channel 118 provides a pathway for pulling the marker wire 120 through and out of the channel 118 such that the exit is proximal to the expandable balloon 108. FIG. 2 illustrates the catheter apparatus 10 of FIG. 1 but with the exit opening 126 positioned distally of the opaque marker 122.

In both examples of FIGS. 1 and 2 the marker wire opening 126 is proximal to the balloon 108 and/or stent delivery device. In other examples, the marker wire channel 118 may extend to a distal end of the balloon have provide an opening distal to the balloon, with a corresponding radiopaque marker located there. Furthermore, in some examples the marker wire channel 118 can have multiple openings 126 for example one of each side of a radiopaque marker to allow for selective positioning of the exit point of the marker wire. In some configurations, multiple openings 126 can be formed along a length of the marker wire channel 118 with radiopaque markers at each opening. This configuration would allow the operator to select how close the marker wire exit point will be to the proximal edge 110 of the balloon 108. By placing the exit point adjacent the balloon 108 as shown in FIGS. 1 and 2, the operator can bring the proximal edge 110 up to an opening in a vessel without the balloon extending from an ostial vessel into a main vessel. By using an exit point further away (in a proximal sense) from the edge 110, the balloon may be adjusted to sit even further inside the ostial vessel and away from the main vessel. Some examples are discussed further below with respect to FIG. 10 for example.

Generally speaking, the marker wire 120 serves to identify the vessel wall and limits advancement of the stent beyond the ostia. At the same time forward pressure on the angioplasty catheter ensures that the stent is adequately aligned with the wall of the parent vessel. This wire may be a standard guidewire used in the art and may be made of nitinol or steel, for example, and may be of a diameter of 0.018", 0.008', 0.014" or any other diameter based on the site for which the device is designed.

The radiopaque markers may be formed of any materials known in the art such as silver, gold, platinum, and tungsten, and that allow the markers to be visible under fluoroscopy, radiography, ultrasonography, magnetic resonance imaging, or other imaging technique. The markers may be formed using known techniques and may be coated onto and/or coated with another biocompatible material other than that of the tubular body 100

In example devices having a therapeutic channel, that channel can be constructed in a fashion that permits capture of any filter device used downstream of the apparatus 10. For example, the apparatus 10 may be used with an emboli protection device, such as a distal filter, distal occlusion device, or proximal occlusion device, and the therapeutic channel may have a single transverse opening ending parallel to the guidewire channel 112 to allow for delivery of a therapeutic agent to the vessel at the location of that transverse opening. Example therapeutic channels within a catheter device are described in U.S. Ser. No. 11/935,131, incorporated by reference above.

The assemblies described herein may be formed through techniques such as blow molding or heat shrinking a thermoplastic film or tubing. Extrusion techniques may be used as well. Suitable materials will be known and include, by way of example, PET, polyesters, nylon, PVC, and polyethylene. The channels 106, 112, and 118 (or lumens) may be formed integrally with the overall tubular body 100, for example, through a single mold process and end capping; or the channels may be separately formed tubular bodies that are fused or otherwise bonded together to form the tubular body 100. When separately formed, the channels may be more easily formed of materials of different composition and having different flexibilit and strength properties. Furthermore, while the channels 112 and 118 are shown in a stacked configuration on an upper side of the channel 106, the channels 112 and 118 may be formed over any portion of the tubular body 100, for example, at opposing (upper and lower) sides or any other relative positions on the tubular body 100.

Although shown in a uniform cross-section, the lumens described may be tapered (necking) or flared toward the distal end and/or toward the proximal end as desired. Further while some inner lumen walls are illustrated as continuous curves (e.g., circular in cross-section), any of the lumen walls may be elliptical in cross-section or take on other shapes, including having planar walls or planar wall portions. The geometry of the lumen may vary across its length as well. Further still the lumens may extend the entire linear length of the tubular body or at least some of the lumens (e.g., the guidewire and inflation lumens) may be helically formed to coil around a central axis, and/or the body of any therapeutic lumen.

Figure 3B:
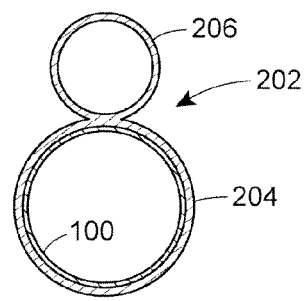

FIG. 3A partially shows another catheter apparatus 200 having similar structure to that of catheter apparatus 10 and therefore using like reference numerals where applicable. The apparatus 10 includes a separate channel for a marker wire that allows a surgeon to align more accurately the proximal end of a balloon or stent; the apparatus 200 does not include a separate channel for a marker wire, but instead, it includes a radiopaque marker 202 that is positioned proximal to the proximal end 110 and includes a base portion 204 that extends around a tubular body 100 to allow for identification by an imaging apparatus (not shown) and a ring channel member 206 that is external to the tubular support 204 and is sized to accept a marker wire threaded there through. FIG. 3B shows a cross-section of the radiopaque marker 202 with integral marker wire channel.

Figure 4:
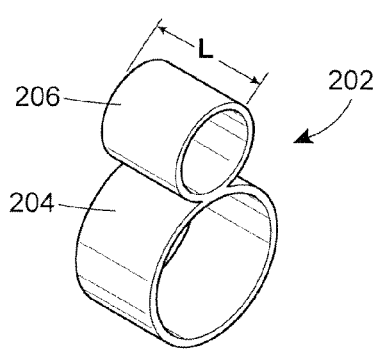
FIG. 4 illustrates a radiopaque marker with integral marker channel in accordance with an example.
Figure 5:
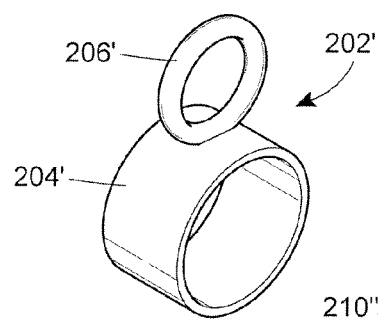
FIG. 5 illustrates a radiopaque marker with integral marker channel in accordance with another example.

FIG. 4 shows an example embodiment of the marker 202 wherein the marker has a length L, which in the illustrated configuration corresponds not only to the length of the support base 204 but also to that of the ring channel 206. It will be understood that the ring channel 206 can have other configurations. FIG. 5 shows a torodial shape marker element 202', which may allow for greater ease of threading in marker wire through the channel 206' by having a rounded edge at an entrance side and an exit side thereof as opposed to a sharper edge resulting from the tubular shape channel 206 of FIG. 4.

Figure 6:
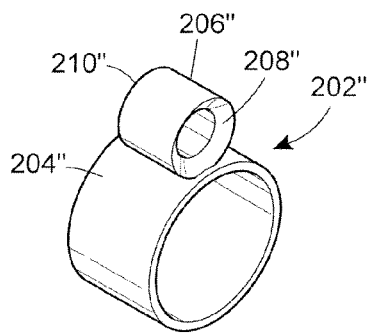
FIG. 6 illustrates a radiopaque marker with integral marker channel in accordance with another example.

FIG. 6 shows a configuration where the ring channel 206'' has a first end 208'' and a second end 210'' that each has a beveled corner shape thereby combining the elongated length of the configuration in FIG. 4 with the tapered or rounded edge of FIG. 5.

Figure 7:
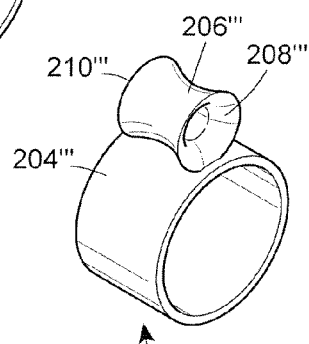
FIG. 7 illustrates a radiopaque marker with integral marker channel in accordance with another example.

FIG. 7 illustrates yet another type of radiopaque marker 202 similar to that of FIG. 6, but with a saddle shape formed by the first end 208''' and the second end 210'''.

For configurations like that of FIGS. 5-7, the entrance and exit angles for the edges (whether tapered or rounded or otherwise), may be adjusted to steeper or less steep levels to allow for greater freedom of movement of the marker wire as it exists the marker. In applications such as those discussed with respect to FIG. 10, for example, the marker may be designed such that the marker wire exists while still being biased against an main vessel wall which will allow the marker wire to act as a backstop guide as the catheter's guidewire is pulled through the blocked, ostial vessel. In other examples, angles may be chosen that allow the marker wire to fold back on itself without such biasing.

Figure 8:
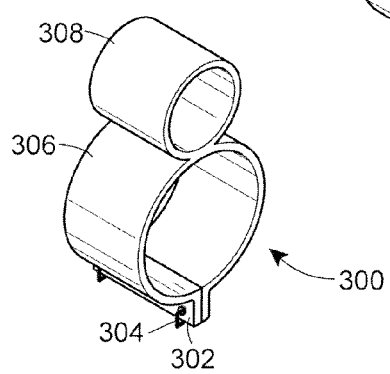
FIG. 8 illustrates a radiopaque marker with integral marker channel in accordance with another example.

FIG. 8 illustrates yet another configuration of a radiopaque member 300, which includes an external clip 302 that may be used to mount the marker around the tubular body 100. The external clip 302 has interlocking snaps 304 for securing the external clip to the channel body 200. The radiopaque marker 300 is shown with a support portion 306 that when attached surrounds the entire circumference of the tubular body 100 and also includes a ring channel 308 that can take any of the forms described herein, by way of example.

Returning to FIG. 3A, the catheter apparatus 200 also includes a radiopaque marker 212 positioned distally to the edge 111 and used for marking that edge 111. Although the marker 212 is illustrated as merely a marker for purposes of radiological imaging identification purposes, the marker 212 may take the form of any of the markers described herein.

Figure 9:
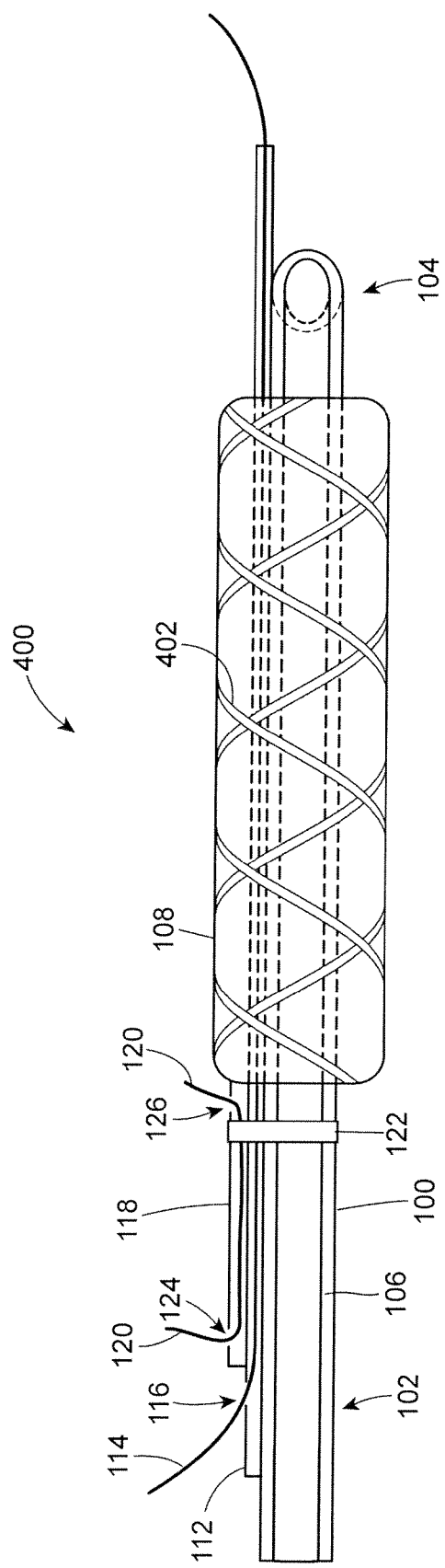
FIG. 9 illustrates a catheter apparatus similar to that of FIG. 2 and having a stent in a non-deployed position.

FIG. 9 illustrates an example stent apparatus 400 similar to the apparatus 10 and apparatus 200 therefore like reference numerals are used. The apparatus 400 includes a deployable stent 402 shown in a non-deployed position surrounding the balloon 108. That stent 402 is dilated by the inflation of the balloon 108 in the illustrated example. It will be appreciated that in other examples a self-expanding stent may be used instead of the balloon 108, if there is one, allowing the balloon 108 to be used for angioplasty clearance of detritus only.

Figure 10:
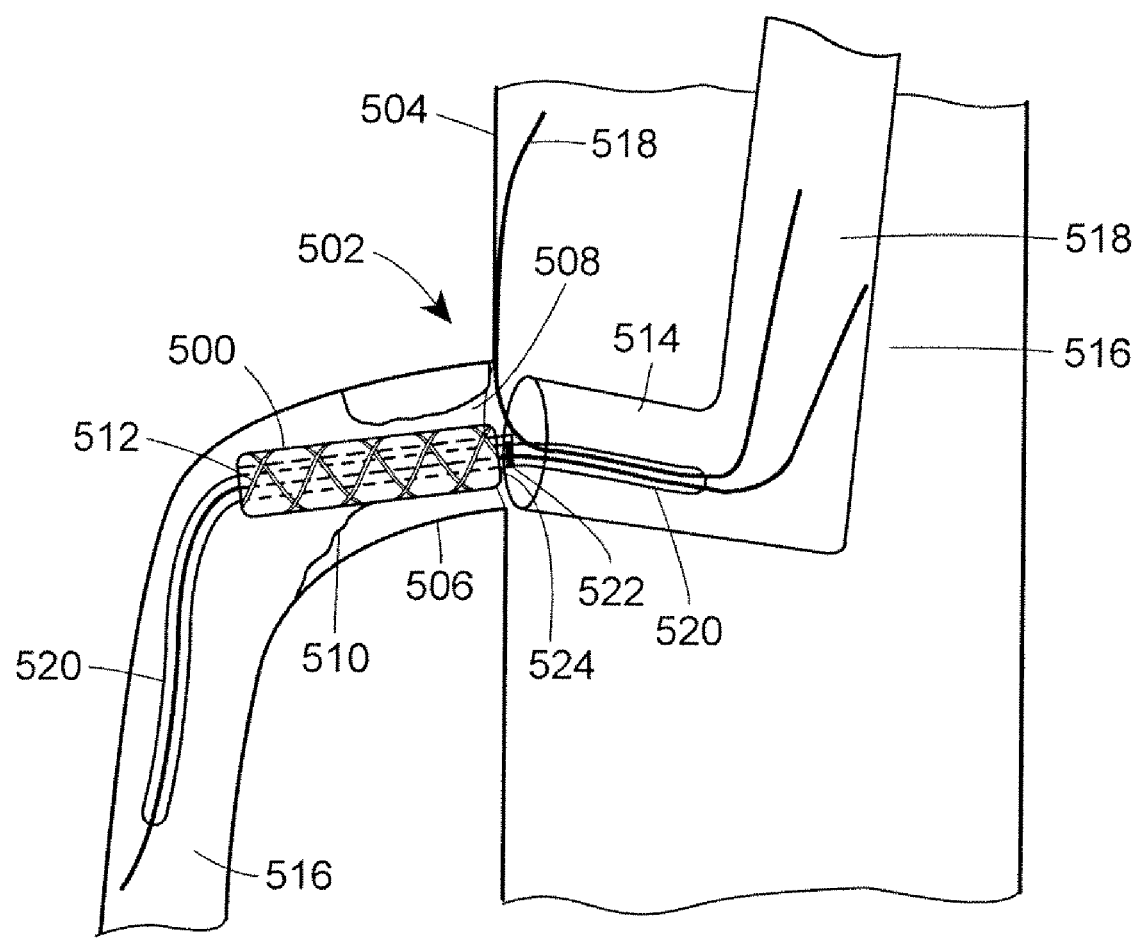
FIG. 10 illustrates an aorto ostial lesion which has been engaged with a guiding catheter and a stent mounted on the balloon angioplasty apparatus and in which a guidewire and a marker wire has been inserted.

FIG. 10 illustrates an example implementation procedure for inserting a catheter device 500 to a bifurcation point 502 for a major vessel 500 and an ostial vessel 506 that includes ostial regions 508 and 510 forming an ostial stenosis situation. The catheter apparatus 500 may be any of those described above (including for example apparatuses 10, 200, or 400) and in the illustrated example includes a deployable stent 512.

The catheter apparatus 500 is positioned in the main vessel 504 by a delivery tube 514 having an elongated extent in a corner configuration. A guidewire 516 is shown and extends from the delivery mechanism 514 through the body 500 and extending along the ostial or minor vessel 506 and serves as a standard catheter guidewire. For convenience, only a portion of a tubular catheter body is shown.

Separately, and in accordance with the examples herein, a marker wire 518 extends along a tubular body 520 having a radiopaque marker 522 that may be used in accordance with the examples discussed above. The marker wire 518 allows a surgeon to use the guidewire to fully insert the catheter apparatus 500 into the ostial vessel 506, but also provides a separate mechanism by which the surgeon can ensure that a proximal end 524 of the stent 512 is flush or near flush with the opening of the ostial vessel 506. For example, the marker wire 518, being semi-rigid, abuts against an inner wall of the main vessel 504 (e.g., an aortic vessel), thereby providing a stop that allows the proximal end 524 to be flush with the ostial opening so that the stent 512 does not extend into the main vessel 504. The surgeon is able to pull on the marker wire 518 and the catheter guidewire 516 independently until the desired alignment is achieved and the apparatus 500, more particularly the stent 512, is prevented from extending out into the major vessel region 504. The configuration shown includes the tubular body 520 having the marker wires 518 extending through marker wire channels not numbered. However, it would be appreciated that the configuration shown may be achieved by a radiopaque marker that itself defines a ring channel for a marker wire 518 and would be external to the tubular body 520, as discussed above.

FIG. 10 provides an example application of a catheter device. The devices described herein may be used as delivery catheters for other in-vessel devices such as a laser or mechanical atherectomy catheter or an ultrasonic or laser plaque modifying/ablation device. Such devices may be combined with the catheters described herein for operation within the vessel and before, during, or after therapeutic delivery, or aspiration.

Figure 11:
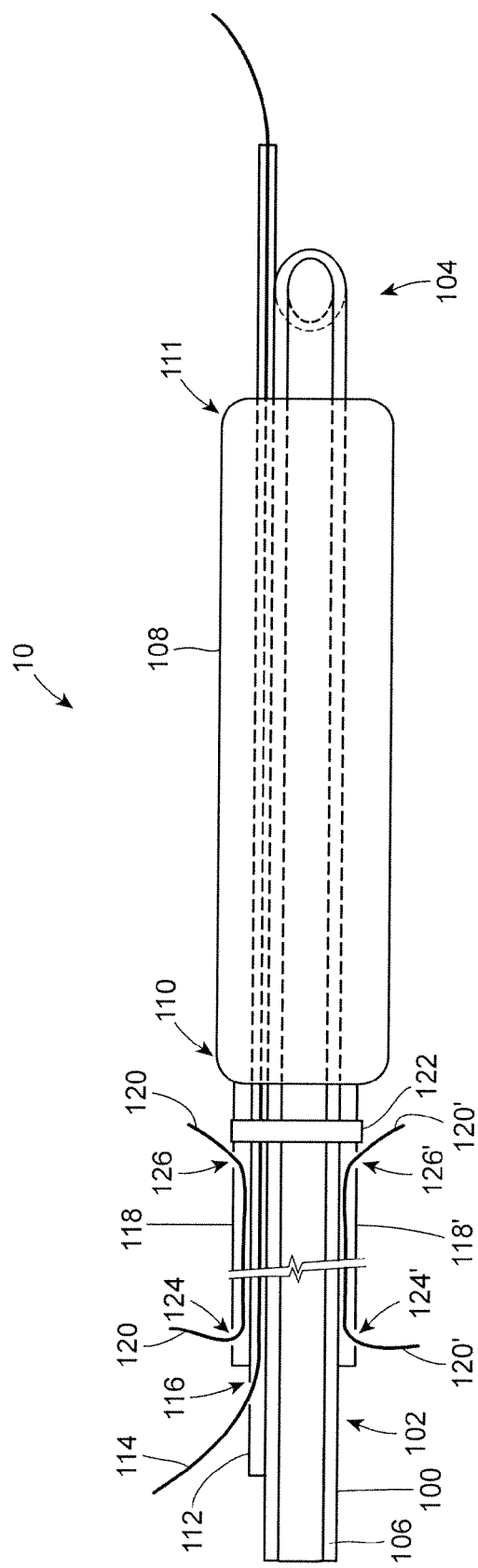
FIG. 11 illustrates a catheter apparatus similar to that of FIG. 1, but having two opposing marker wires and corresponding channels.

Further still, as shown in FIG. 11, multiple marker wires may be used to assistant in positioning a catheter device. FIG. 11 is the same as FIG. 1, but with a second marker wire 120' like that of marker wire 120, but on an opposing side of the tubular body 100 and allowing a surgeon to control not only the lateral position of catheter device 10' but the horizontal (or top/bottom position in the illustrated drawing) position as well. The use of a second, opposing marker may be extended to any of the examples described herein. Furthermore, while the second marker wire 120' is shown directly opposing the first marker wire 120, the second marker wire 120' and corresponding marker wire channel 118' may be positioned anywhere about the tubular body 100, and may even be positioned on the opposite side of the balloon 110 adjacent the distal end 111. FIG. 11 is shown for example purposes, and using like reference numerals to that of FIG. 1.

Although certain apparatus constructed in accordance with the teachings of the invention have been described herein, the scope of coverage of this patent is not limited thereto. On the contrary, this patent covers all embodiments of the teachings of the invention fairly falling within the scope of the appended claims either literally or under the doctrine of equivalents.

What is claimed:

1. A catheter device for administering a stent in an ostial vessel, the catheter device comprising:
   an expandable balloon have a proximal end and a distal end, the expandable balloon having an inflation channel extending past the proximal end for delivering inflation pressure to the expandable balloon;
   a catheter guidewire channel extending from a proximal end of the catheter device to a distal end of the catheter device, a distal end of the catheter guidewire channel extending past the distal end of the expandable balloon and providing a pathway for a catheter guidewire; and
   a radiopaque marker positioned proximal to the proximal end of the expandable balloon, the radiopaque marker having a base portion that extends around a tubular body of the catheter device and a ring channel coupled to the base portion, the ring channel being external to the tubular body of the catheter device, and the ring channel defining an opening for receiving a marker wire proximal to the expandable balloon, wherein the catheter guidewire channel is disposed external to the opening of the ring channel, wherein the base portion of the radiopaque marker is coupled to the ring channel of the radiopaque marker to form a figure-eight shape when viewed along a longitudinal axis of the catheter device.

2. The catheter device of claim 1, wherein the ring channel extends the length of the radiopaque marker.

3. The catheter device of claim 1, wherein the ring channel comprises a guided first end and guided second end that together at least partially form a saddle shape.

4. The catheter device of claim 1, wherein the radiopaque marker comprises an external clamp for mounting to a shaft of the catheter device.

5. The catheter device of claim 4, wherein the external clamp has interlocking snaps for securing the external clamp to the shaft of the catheter device.

6. The catheter device of claim 1, further comprising another radiopaque marker positioned distally of the expandable balloon.

7. The catheter device of or claim 1, further comprising an expandable stent surrounding at least a portion of the expandable balloon.

8. The catheter device of claim 1, wherein the radiopaque marker is disposed on an exterior of the tubular body of the catheter device.

9. The catheter device of claim 1, wherein both the base portion and the ring channel have a substantially circular cross-sectional shape.

* * * * *

UNITED STATES PATENT AND TRADEMARK OFFICE
CERTIFICATE OF CORRECTION

PATENT NO. : 8,287,585 B2
APPLICATION NO. : 12/344034
DATED : October 16, 2012
INVENTOR(S) : Gurm Page 1 of 1

It is certified that error appears in the above-identified patent and that said Letters Patent is hereby corrected as shown below:

In the Claims

In Column 10, Line 28, in Claim 7, delete "of or" and insert -- of --, therefor.

Signed and Sealed this
Twenty-seventh Day of January, 2015

Michelle K. Lee
*Deputy Director of the United States Patent and Trademark Office*